US008696689B2

(12) United States Patent
Tuval et al.

(10) Patent No.: US 8,696,689 B2
(45) Date of Patent: Apr. 15, 2014

(54) MEDICAL SUTURING DEVICE AND METHOD FOR USE THEREOF

(75) Inventors: Yosi Tuval, Netanya (IL); Raphael Benary Benary, Tel Aviv (IL)

(73) Assignee: Medtronic Ventor Technologies Ltd., Netanya (IL)

( * ) Notice: Subject to any disclaimer, the term of this patent is extended or adjusted under 35 U.S.C. 154(b) by 1145 days.

(21) Appl. No.: 12/050,184

(22) Filed: Mar. 18, 2008

(65) Prior Publication Data

US 2009/0240264 A1    Sep. 24, 2009

(51) Int. Cl.
*A61B 17/04*        (2006.01)
(52) U.S. Cl.
USPC .......................................................... 606/144
(58) Field of Classification Search
USPC .................... 606/232, 139, 144, 148, 222
See application file for complete search history.

(56) References Cited

U.S. PATENT DOCUMENTS

| | | | |
|---|---|---|---|
| 5,281,236 A * | 1/1994 | Bagnato et al. | 606/139 |
| 5,356,424 A * | 10/1994 | Buzerak et al. | 606/223 |
| 5,411,552 A | 5/1995 | Andersen et al. | |
| 5,500,014 A | 3/1996 | Quijano et al. | |
| 5,562,685 A * | 10/1996 | Mollenauer et al. | 606/144 |
| 5,569,269 A * | 10/1996 | Hart et al. | 606/144 |
| 5,575,818 A | 11/1996 | Pinchuk | |
| 5,609,626 A | 3/1997 | Quijano et al. | |
| 5,695,498 A | 12/1997 | Tower | |
| 5,782,809 A | 7/1998 | Umeno et al. | |
| 5,817,126 A | 10/1998 | Imran | |
| 5,824,061 A | 10/1998 | Quijano et al. | |
| 5,855,601 A | 1/1999 | Bessler et al. | |
| 5,957,949 A | 9/1999 | Leonhardt et al. | |
| 5,972,001 A * | 10/1999 | Yoon | 606/139 |
| 5,997,573 A | 12/1999 | Quijano et al. | |
| 6,042,607 A | 3/2000 | Williamson, IV | |
| 6,110,201 A | 8/2000 | Quijano et al. | |
| 6,159,239 A | 12/2000 | Greenhalgh | |
| 6,171,335 B1 | 1/2001 | Wheatley et al. | |
| 6,200,336 B1 | 3/2001 | Pavcnik et al. | |
| 6,338,735 B1 | 1/2002 | Stevens | |
| 6,425,916 B1 | 7/2002 | Garrison et al. | |
| 6,440,164 B1 | 8/2002 | DiMatteo et al. | |

(Continued)

FOREIGN PATENT DOCUMENTS

| | | |
|---|---|---|
| WO | 2005/044079 | 5/2005 |
| WO | 2008/004147 | 4/2008 |
| WO | 2008-138584 | 11/2008 |
| WO | 2009-140545 | 11/2009 |

OTHER PUBLICATIONS

U.S. Appl. No. 12/427,395, filed Apr. 21, 2009.

*Primary Examiner* — Tuan V Nguyen (57) ABSTRACT

A suturing device for use with a delivery catheter in a transcatheter procedure, for closing an opening formed in the body. The suturing device includes: a spiral needle having a central core, a proximal end, and a distal end. The distal end terminates in a sharp point for cutting a spiral passageway through body tissue surrounding the opening that is to be closed. The device also includes a guide wire having a suture eye at one end thereof for receiving suture thread after the guide wire has been advanced through the hollow central core of the spiral needle. The device further includes driving means, for allowing advancing and retracting of the spiral needle and guide wire with respect to the catheter, and for allowing connecting between the suture thread and the suture eye of the guide wire.

9 Claims, 11 Drawing Sheets

(56) References Cited

U.S. PATENT DOCUMENTS

| | | |
|---|---|---|
| 6,454,799 B1 | 9/2002 | Schreck |
| 6,458,153 B1 | 10/2002 | Bailey et al. |
| 6,468,303 B1 | 10/2002 | Amplatz et al. |
| 6,482,228 B1 | 11/2002 | Norred |
| 6,494,909 B2 | 12/2002 | Greenhalgh |
| 6,554,845 B1 * | 4/2003 | Fleenor et al. ............... 606/148 |
| 6,558,314 B1 | 5/2003 | Adelman et al. |
| 6,652,578 B2 | 11/2003 | Bailey et al. |
| 6,830,584 B1 | 12/2004 | Seguin |
| 6,830,585 B1 | 12/2004 | Artof |
| 6,875,231 B2 | 4/2005 | Anduiza et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,936,066 B2 | 8/2005 | Palmaz et al. |
| 6,939,365 B1 | 9/2005 | Fogarty et al. |
| 7,097,659 B2 | 8/2006 | Woolfson et al. |
| 7,101,396 B2 | 9/2006 | Artof et al. |
| 7,104,949 B2 * | 9/2006 | Anderson et al. ............... 600/30 |
| 7,105,016 B2 | 9/2006 | Shiu et al. |
| 7,147,663 B1 | 12/2006 | Berg et al. |
| 7,153,324 B2 | 12/2006 | Case et al. |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,329,278 B2 | 2/2008 | Seguin |
| 7,338,520 B2 | 3/2008 | Bailey et al. |
| 7,429,269 B2 | 9/2008 | Schwammenthal et al. |
| 7,442,204 B2 | 10/2008 | Schwammenthal et al. |
| 7,635,386 B1 | 12/2009 | Gammie et al. |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2002/0151970 A1 | 10/2002 | Garrison et al. |
| 2003/0130729 A1 | 7/2003 | Paniagua et al. |
| 2003/0149476 A1 | 8/2003 | Damm et al. |
| 2003/0149478 A1 | 8/2003 | Figulla et al. |
| 2004/0034411 A1 | 2/2004 | Quijano et al. |
| 2004/0049266 A1 | 3/2004 | Anduiza et al. |
| 2004/0098112 A1 | 5/2004 | DiMatteo et al. |
| 2004/0106976 A1 | 6/2004 | Bailey et al. |
| 2004/0138742 A1 | 7/2004 | Myers et al. |
| 2004/0210304 A1 | 10/2004 | Seguin et al. |
| 2004/0225354 A1 | 11/2004 | Allen |
| 2005/0010246 A1 | 1/2005 | Streeter |
| 2005/0015112 A1 | 1/2005 | Cohn et al. |
| 2005/0027348 A1 | 2/2005 | Case et al. |
| 2005/0038316 A1 | 2/2005 | Taylor |
| 2005/0055088 A1 | 3/2005 | Liddicoat et al. |
| 2005/0075717 A1 | 4/2005 | Nguyen |
| 2005/0075719 A1 | 4/2005 | Bergheim |
| 2005/0075730 A1 | 4/2005 | Myers |
| 2005/0075731 A1 | 4/2005 | Artof |
| 2005/0085900 A1 | 4/2005 | Case et al. |
| 2005/0096734 A1 | 5/2005 | Majercak et al. |
| 2005/0096735 A1 | 5/2005 | Hojeibane et al. |
| 2005/0119688 A1 | 6/2005 | Bergheim |
| 2005/0261759 A1 | 11/2005 | Lambrecht et al. |
| 2005/0283962 A1 | 12/2005 | Boudjemline |
| 2006/0052867 A1 | 3/2006 | Revuelta et al. |
| 2006/0074484 A1 | 4/2006 | Huber |
| 2006/0100685 A1 | 5/2006 | Seguin et al. |
| 2006/0200047 A1 | 9/2006 | Galdonik et al. |
| 2006/0206202 A1 | 9/2006 | Bonhoefer et al. |
| 2006/0247570 A1 | 11/2006 | Pokorney |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2007/0005129 A1 | 1/2007 | Damm et al. |
| 2007/0005131 A1 | 1/2007 | Taylor |
| 2007/0078510 A1 | 4/2007 | Ryan |
| 2007/0088431 A1 | 4/2007 | Bourang et al. |
| 2007/0123840 A1 | 5/2007 | Cox |
| 2007/0233228 A1 | 10/2007 | Eberhardt et al. |
| 2007/0233237 A1 | 10/2007 | Krivoruchko |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2008/0009940 A1 | 1/2008 | Cribier |
| 2008/0015671 A1 | 1/2008 | Bonhoeffer |
| 2008/0048656 A1 | 2/2008 | Tan |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082166 A1 | 4/2008 | Styrc et al. |
| 2008/0154356 A1 | 6/2008 | Obermiller et al. |
| 2008/0161826 A1 | 7/2008 | Guiraudon |
| 2008/0228254 A1 | 9/2008 | Ryan |
| 2008/0228263 A1 | 9/2008 | Ryan |
| 2008/0234797 A1 | 9/2008 | Styrc |
| 2008/0255660 A1 | 10/2008 | Guyenot et al. |
| 2008/0255661 A1 | 10/2008 | Straubinger et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0138079 A1 | 5/2009 | Tuval et al. |
| 2009/0171447 A1 | 7/2009 | VonSegesser et al. |
| 2009/0216313 A1 | 8/2009 | Straubinger et al. |
| 2009/0222026 A1 | 9/2009 | Rothstein et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287183 A1 | 11/2009 | Bishop et al. |
| 2010/0004739 A1 | 1/2010 | Vesely |
| 2010/0094411 A1 | 4/2010 | Tuval et al. |
| 2010/0131054 A1 | 5/2010 | Tuval et al. |
| 2010/0137979 A1 | 6/2010 | Tuval et al. |

\* cited by examiner

MEDICAL SUTURING DEVICE AND METHOD FOR USE THEREOF

FIELD OF THE INVENTION

The present invention relates generally to the field of medical suturing devices. More specifically, the present invention relates to a suturing device that is adapted for use in a transcatheter procedure for closing a hole formed in the body.

BACKGROUND OF THE INVENTION

Recent advances in medical technology have made it possible to implant a prosthetic valve device into a native heart valve orifice using a transcatheter procedure. The use of a transcatheter procedure instead of open-heart surgery has many advantages, among them, a significant reduction in the risk, cost, and recovery time that is traditionally associated with heart surgery.

In one such transcatheter valve implantation procedure, a delivery catheter is advanced through an opening formed in the apex of the heart to the site where the prosthetic valve is to be implanted. A prosthetic valve device used in such a procedure is disclosed in U.S. Patent Application No. Application 2006/0149360 to Schwammenthal, et al. which describes an expandable stent-mounted valve specially adapted for implantation into a native valve orifice. The stent-mounted valve is loaded in a compressed state inside of the delivery catheter. When the implantation site is reached, the stent-mounted valve is released from the catheter and automatically assumes the proper position in the valve so as to restore proper blood flow through the valve.

Following implantation of the valve, it is necessary to close the opening which was formed in the heart apex. It would be desirable to perform such closing in conjunction with the transcatheter procedure, so that a separate procedure would not be required.

A variety of devices are known in the art for suturing an opening formed in a body lumen. For example, Japanese Patent No. 2001198132 relates to a suturing device for closing an opening following an operation. Suturing after a lesion is incised is made possible by rotating a hollow and spiral suturing needle with curvature around the center of the curvature as a shaft.

U.S. Pat. No. 5,626,613 to Schmieding et al., relates to a corkscrew suture anchor having a spiral-shaped body with a hollow central core, a distal end, and a proximal end. The distal end of the spiral body terminates in a sharp point, and the proximal end of the spiral-shaped body has an eye for receiving suture.

U.S. Pat. No. 6,916,333, also to Schmieding et al., relates to a corkscrew suture anchor has a continuous thread spiraling around a tapering central core. At the distal end, the suture anchor terminates in a rounded point. At the proximal end of the suture anchor is an eye for receiving suture.

Russian Patent No. 2119771 relates to a device having a casing with an unmovable working lip, movable working lip and handles. A mechanism for suturing is enclosed in the casing.

Korean Patent Disclosure No. 20040075834 relates to a laparoscopic suture instrument for allowing ease of surgery by removing a hinge between devices for holding suture needles and integrating suture needles and a handle.

None of the aforementioned prior art references provide a suturing device that is suitable for use in conjunction with a transcatheter procedure and specifically, for closing an opening formed in the apex of the heart following implantation of a prosthetic valve device.

SUMMARY OF THE INVENTION

Accordingly, it is a principal object of the present invention to overcome the disadvantages of the prior art and provide a suturing device that is adapted for use with a delivery catheter, for closing an opening formed in the body. The opening that is to be closed may be any type of opening, such as an opening formed during a medical procedure in order to reach a specific site in the body, or an unwanted opening in any body passageway or organ, which formed on its own.

In accordance with a preferred embodiment of the present invention, there is provided a suturing device for use with a delivery catheter in a transcatheter procedure, for closing an opening formed in body tissue, said suturing device comprising;

(a) a spiral needle having a hollow central core, a proximal end, and a distal end, said distal end terminating in a sharp point forming an aperture of said hollow core, for cutting a spiral passageway through body tissue surrounding said opening to be closed;

(b) a guide wire having a suture eye at one end thereof for receiving suture thread at said distal end after said guide wire has been advanced through said hollow central core of said spiral needle, and (e) driving means, for rotatably advancing and retracting said spiral needle and guide wire with respect to said catheter, such that when said device is rotatably advanced with respect to said body tissue opening, a connection can be made between said suture thread and said suture eye of said guide wire, thus enabling formation of a spiral suture as said device is rotatably retracted.

The suturing device of the present invention is adapted for being introduced to the closure site using a delivery catheter. The catheter acts as a guide for allowing the surgeon to control the suturing procedure. It will be appreciated that while the present invention is described as being useful in conjunction with a delivery catheter in a transcatheter procedure, it can be used in an independent procedure as well. In addition to a conventional delivery catheter, any suitable substantially hollow and tubular body adapted for being advanced through body tissue, such as but not limited to a trocar, may be employed in the suturing device in order to facilitate reaching the suturing site and performing of the suturing process (to be described further hereinbelow).

In a preferred embodiment of the present invention, the suturing device is adapted for use for closing an opening formed in the apex of the heart during a transapical valve implantation procedure. Using the suturing device of the present invention, closure of the apex opening simply becomes one of the last steps in the valve implantation procedure, before the delivery catheter is withdrawn from the body. Thus, the need for a separate procedure for closing the opening is avoided. This is a great benefit, both for the surgeon and for the patient. It will be appreciated by those skilled in the art that the device of the present invention may be useful for other catheter-based procedures as well, for closing an opening formed in the body.

The present invention thus relates to a suturing device for use with a delivery catheter in a transcatheter procedure, for closing an opening formed in the body. The suturing device comprises: a spiral needle having a central core, a proximal end, and a distal end. The distal end terminates in a sharp point for cutting a spiral passageway through body tissue surrounding the opening that is to be closed. The device also includes a guide wire having a suture eye at one end thereof for receiving suture thread after the guide wire has been advanced through the hollow central core of the spiral needle. The device further includes driving means, for allowing advancing and retracting of the spiral needle and guide wire with respect to the catheter, and for allowing connecting between the suture thread and the suture eye of the guide wire.

The present invention also relates to a method for closing an opening formed in the body using a transcatheter procedure, comprising;

(a) providing a spiral needle mountable around the exterior of a delivery catheter, the spiral needle having a central core, a proximal end, and a distal end, the distal end terminating in a sharp point for cutting a spiral passageway through body tissue surrounding the opening to be closed;
(b) providing driving means coupled to the spiral needle for driving said spiral needle with respect to the catheter;
(c) loading and advancing the spiral needle on the catheter to the site of an opening to be sutured;
(d) cutting a spiral passageway through body tissue surrounding the opening using said spiral needle;
(e) inserting a guide wire through the spiral needle, the guide wire having a suture hook at the end thereof for receiving suture thread;
(f) introducing the first end of a suture thread through the inside of the catheter until said first end becomes exposed at the end of the catheter;
(g) connecting the first end of the suture thread to the suture hook of the guide wire, preferably via counter-rotation of the spiral needle using the driving means, and;
(h) retracting the guide wire and the suture thread connected thereto back through the spiral passageway;
(i) withdrawing the spiral needle from the suture site, and;
(j) withdrawing the delivery catheter or trocar, and
(k) joining the first end of the suture thread to the second end of the suture thread, preferably by tying the two ends in a surgical knot In some preferred embodiments, a flexible tube is advanced through the catheter prior to insertion of the suture thread. Then, the suture thread is advanced through the flexible tube inside of the catheter, until the end of the suture thread is exposed at the end of the catheter. If the delivery catheter has a central shaft, this may also be employed for advancement of the suture thread therethrough.

In some instances, step (g) is performed in two steps: first, the guide wire with the suture thread attached thereto is retracted through the spiral needle; second, the spiral needle is itself retracted and withdrawn from the spiral passageway.

Using the device of the present invention, the risks, and side effects, and recovery time for the suturing procedure are each significantly reduced. The device itself is relatively simple to operate, and allows the surgeon to easily visualize the procedure, using radiology or any other suitable means, while it is being performed. The procedure itself requires only a few steps, and thus is relatively easy to learn to do. Surface suturing, which is currently the most commonly used technique for suturing the heart opening, does not achieve closure throughout the heart apex wall. In contrast, the suturing device of the present invention does achieve this.

Other features and advantages of the present invention will become apparent from the following drawings and description.

BRIEF DESCRIPTION OF THE DRAWINGS

For a better understanding of the invention with regard to the embodiments thereof, reference is made to the accompanying drawings, not to scale, in which like numerals designate corresponding elements or sections throughout and wherein.

DETAILED DESCRIPTION OF THE PREFERRED EMBODIMENTS

It will be appreciated that the description provided is intended only to illustrate and clarify a main preferred embodiment of the present invention. It is in no way meant to limit the scope of the invention, as set out in the claims.

Figure 1:
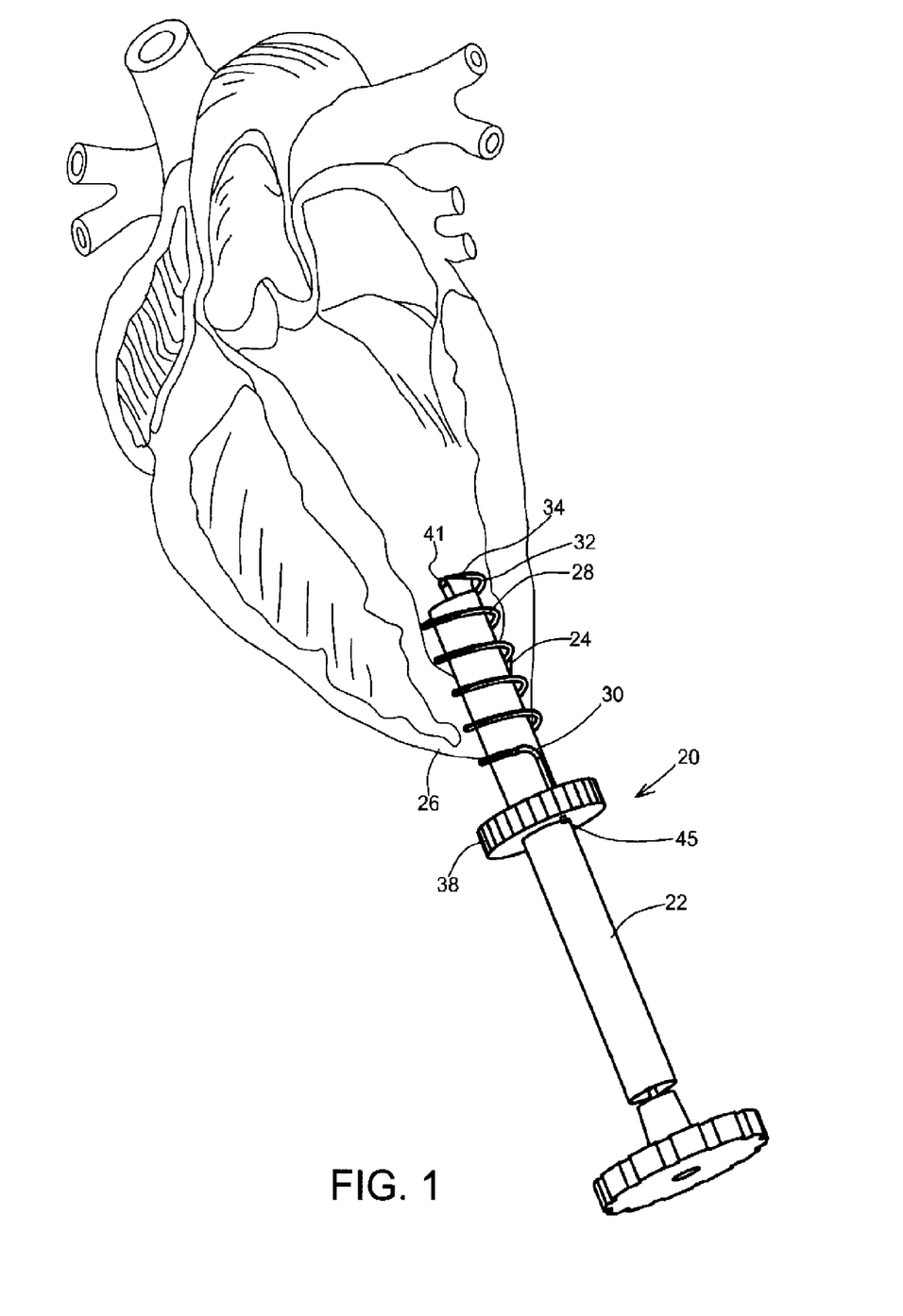
FIG. 1 is a schematic view of a suturing device for closing an opening formed in the apex of the heart, according to a preferred embodiment of the present invention, with the device shown positioned inside of the heart apex opening, in preparation for performing suturing.

Referring now to the drawings, FIG. 1 is a schematic view of a suturing device for closing an opening formed in the apex of the heart, according to a preferred embodiment of the present invention. The device is shown positioned inside of the heart apex opening, in preparation for performing suturing. It is noted that all of the remaining drawings refer to the preferred embodiment which is illustrated generally in FIG. 1.

The suturing device 20 of the present invention comprises a tubular delivery catheter 22. Catheter 22 may be been employed in the performance of another catheter-based procedure (prior to or following suturing), or catheter 22 may be solely used for the performance of suturing using the suturing device of the present invention.

In the example illustrated, suturing device 20 is being employed for closing an opening 24 which was formed in the apex 26 of the heart during a prosthetic valve implantation procedure. It is appreciated that the suturing device of the present invention could be used in a variety of other applications as well.

Suturing device 20 further comprises a spiral needle 28 formed with a hollow interior cross-section and having a proximal end 30 and a distal end 32. Spiral needle 28 terminates in a sharp point 34 for cutting a spiral passageway through body tissue surrounding the opening to be closed. A spiral needle driver 38 is attached for facilitating rotation and advancement of spiral needle 28 around catheter 22.

Figure 2:
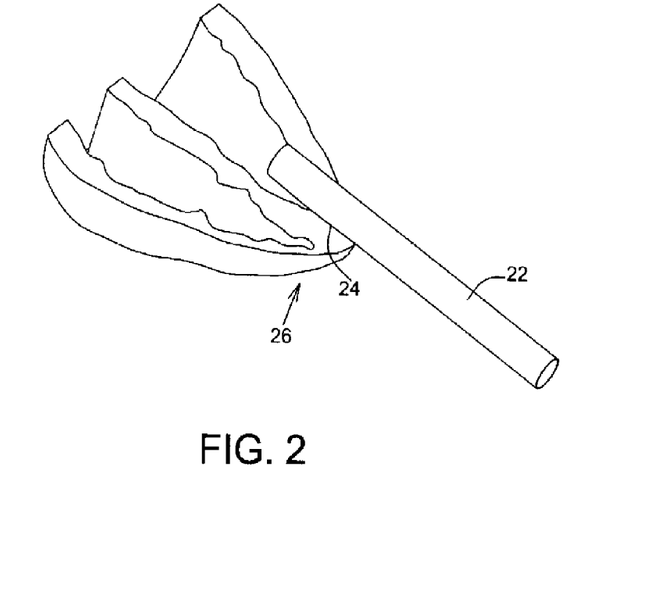
FIG. 2 is a cutaway view of the apex of the human heart, showing a catheter in place inside of the apex opening.
Figure 3:
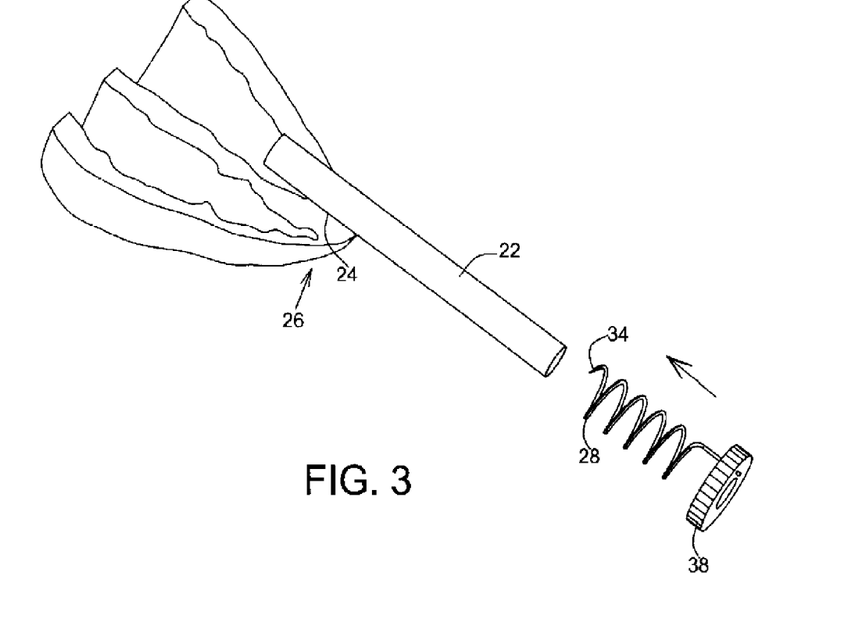
FIGS. 3-6 represent cutaway views of the apex of the human heart, showing the catheter in place inside of the apex opening and showing a spiral needle and driver element as the spiral needle is advanced (via rotation of the driver element) around the catheter so as to cut a spiral passageway through the cardiac tissue surrounding the opening.
Figure 4A:
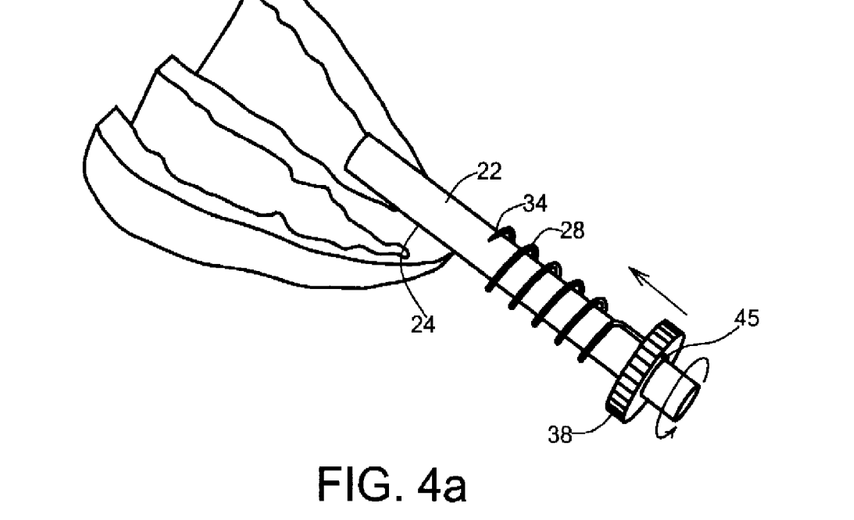
Figure 4B:
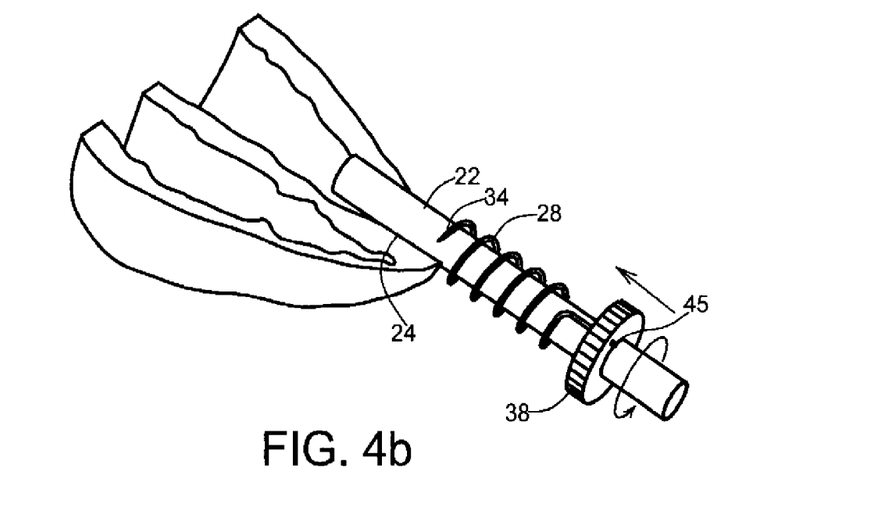
Figure 5:
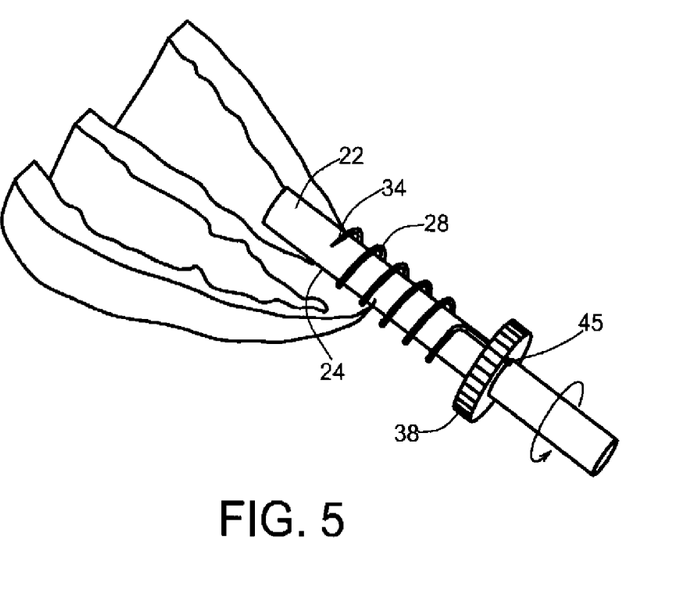
Figure 6:
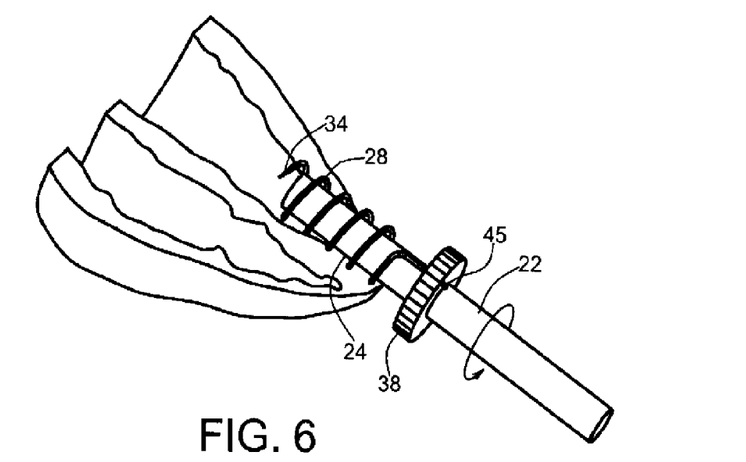

FIG. 2 illustrates catheter 22 positioned inside of the opening 24 formed in heart apex 26 prior to introduction of spiral needle 28 to the suturing site.

In FIGS. 3-6, spiral needle 28 and its attached spiral needle driver 38 are introduced and advanced with respect to catheter 22 by means of rotation of driver 38. Spiral needle 28 is advanced towards opening 24 and sharp point 34 of spiral needle 28 then cuts a spiral shaped passageway through tissue surrounding opening 24.

Figure 7:
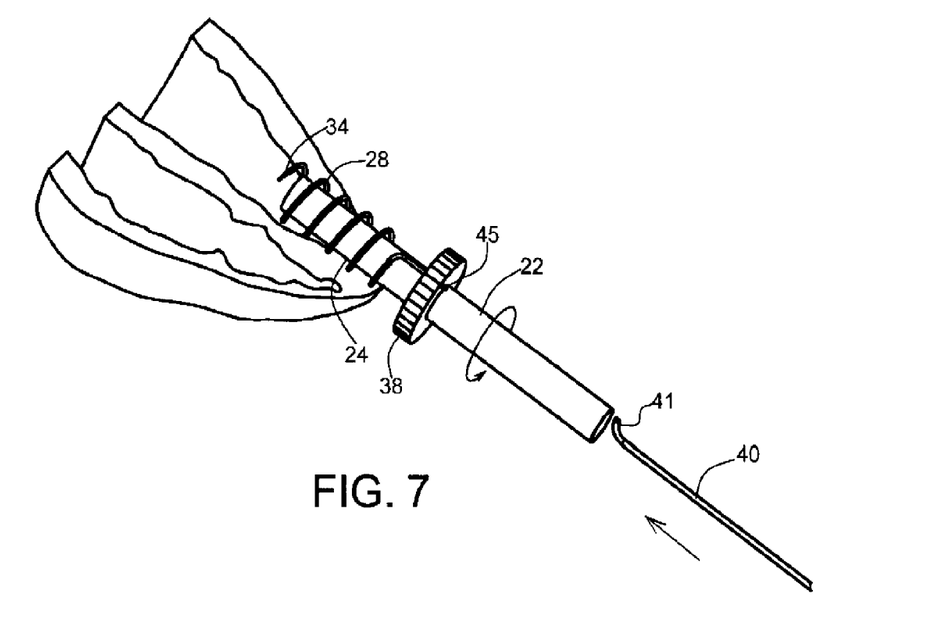
FIG. 7 represents a cutaway view of the apex of the human heart, after the spiral passageway has been cut through the cardiac tissue, and as a flexible tube is being advanced through the interior of the catheter.
Figure 8:
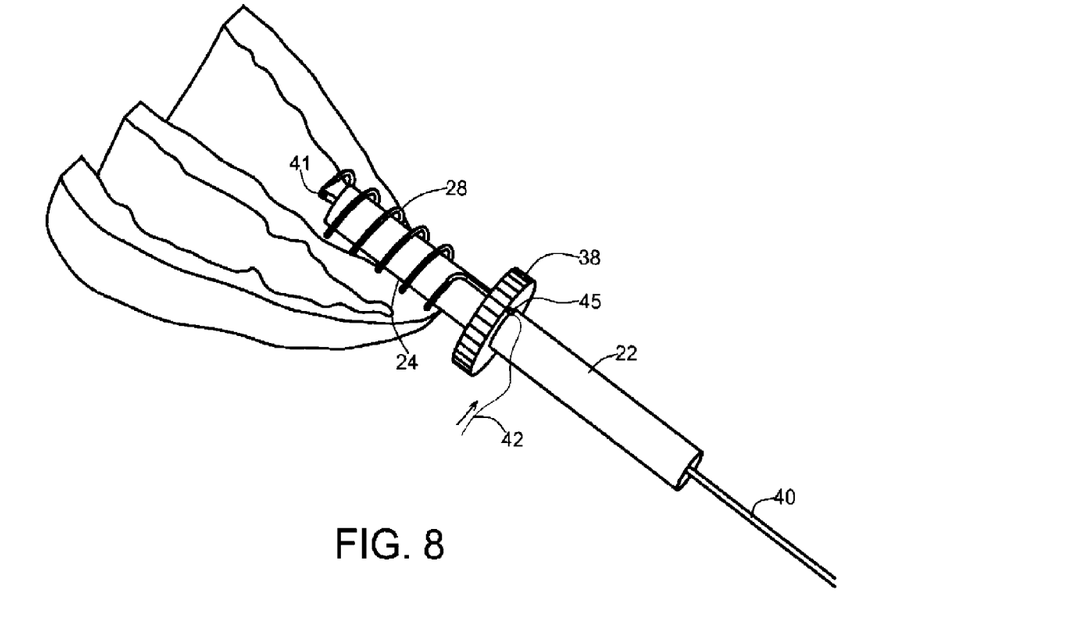
FIGS. 8-9 represent cutaway views of the apex of the human heart, as a guide wire having a suture hook at the end is advanced through the spiral needle.

Next, as seen in FIG. 7, a flexible tube 40 having a curved end 41 is introduced through the interior of catheter 22 until end 41 of flexible tube 40 is seen extending from the end of catheter 22 (see FIG. 8).

Figure 9:
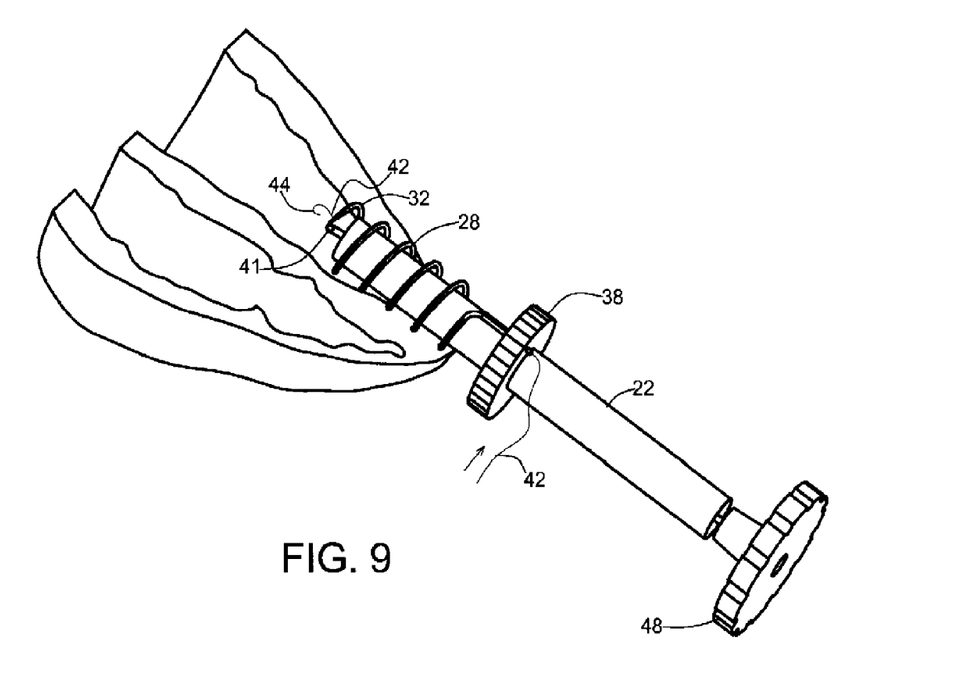

In FIGS. 8 and 9, a guide wire 42 is advanced through the hollow interior of spiral needle 28 from the proximal end 30 thereof until it is exposed at the distal end 32 of spiral needle 28. Guidewire 42 is inserted into the hollow interior of spiral needle 28 via an opening 45 in the spiral needle driver 38 to which the hollow interior is connected. Guide wire 42 has a suture hook 44 at the end thereof.

Figure 10A:
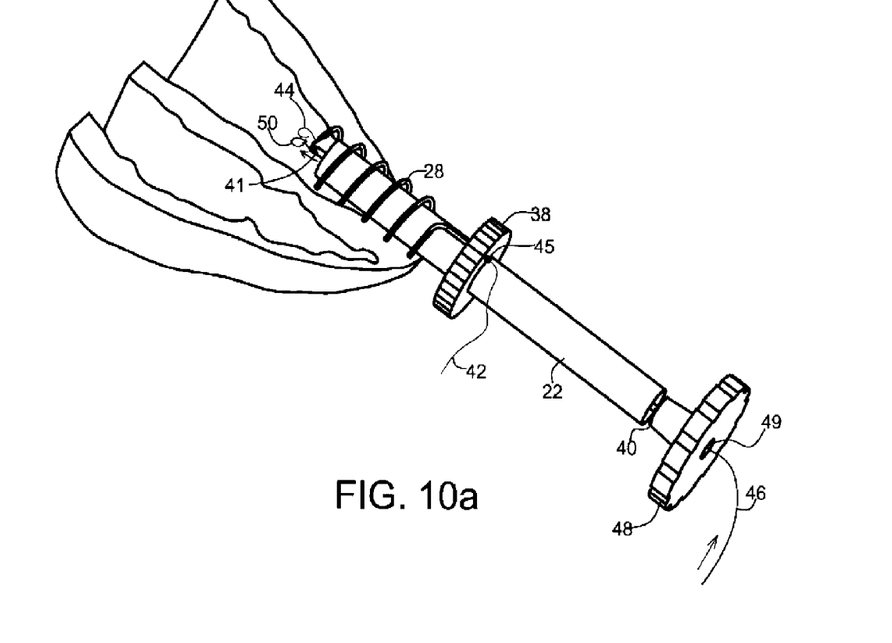
FIGS. 10a-b represent, respectively, a cutaway view of the apex of the human heart, as the end of a suture thread is advanced through the flexible tube inside of the catheter, and an enlarged view thereof.
Figure 10B:
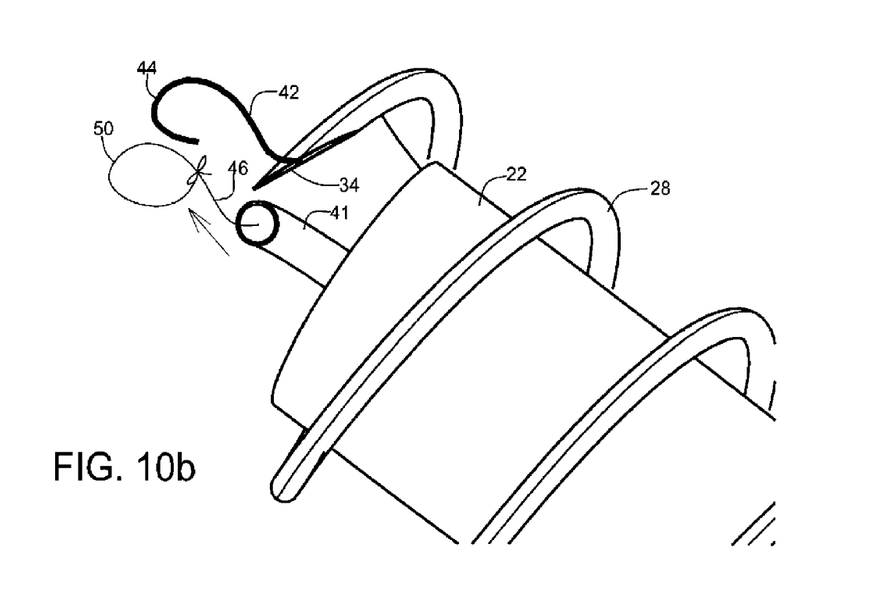

In FIGS. 10a-b, a suture thread 46 is introduced into flexible tube 40 and advanced through catheter 22 via flexible tube 40. A second driver 48 is provided for facilitating advancement of suture thread 46 through tube 40. Suture thread 46 is inserted through an opening 49 in driver 48. Suture thread 46 is advanced until the first end 50 of suture thread 46 is exposed at the end 41 of flexible tube 40. Preferably, a loop is formed at first end 50 of suture thread 46.

Figure 11A:
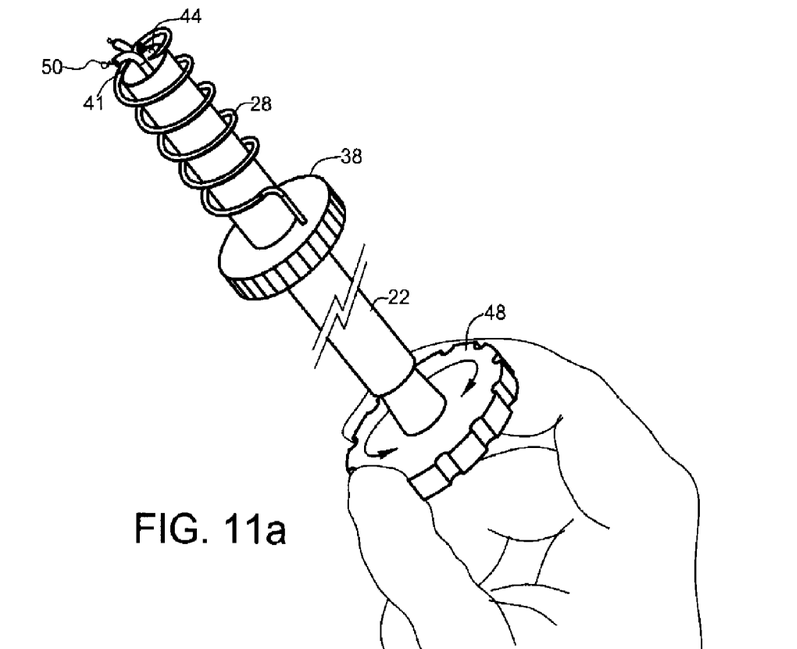
FIGS. 11a-11b represent cutaway views of the apex of the human heart, as the suture thread is becoming hooked onto the suture hook of the guidewire.
Figure 11B:
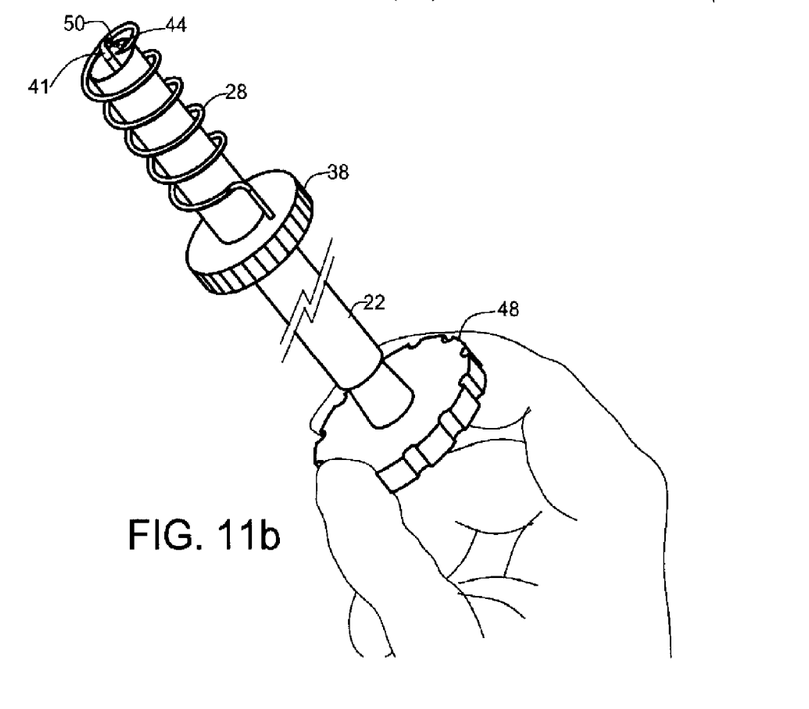
Figure 12A:
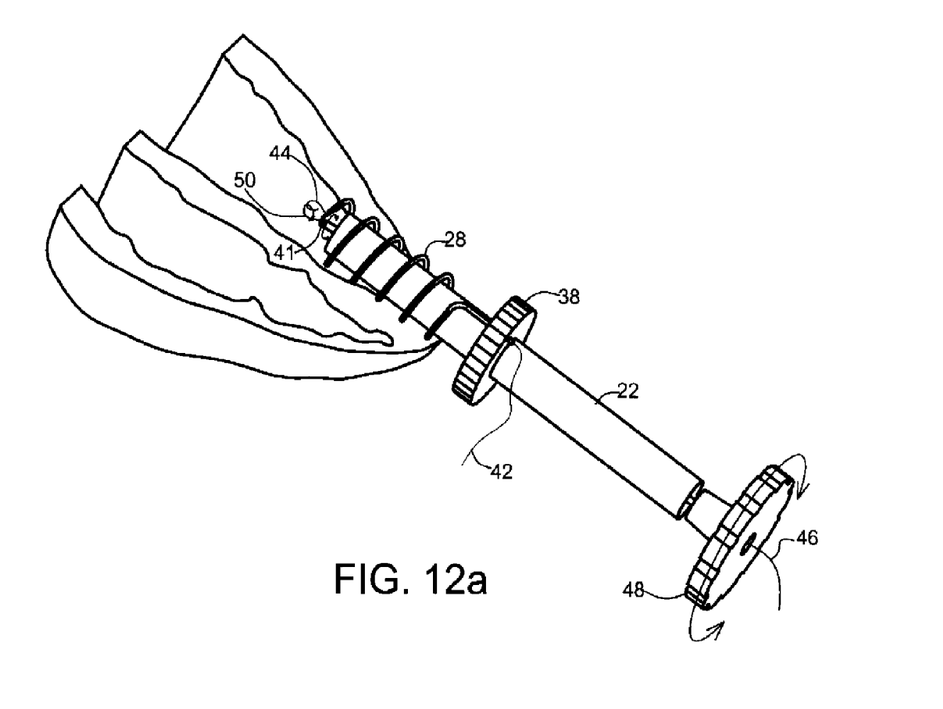
FIGS. 12a-b are respectively, a schematic view of the suturing device, after the suture thread has become hooked onto the suture hook, and an enlarged view thereof.
Figure 12B:
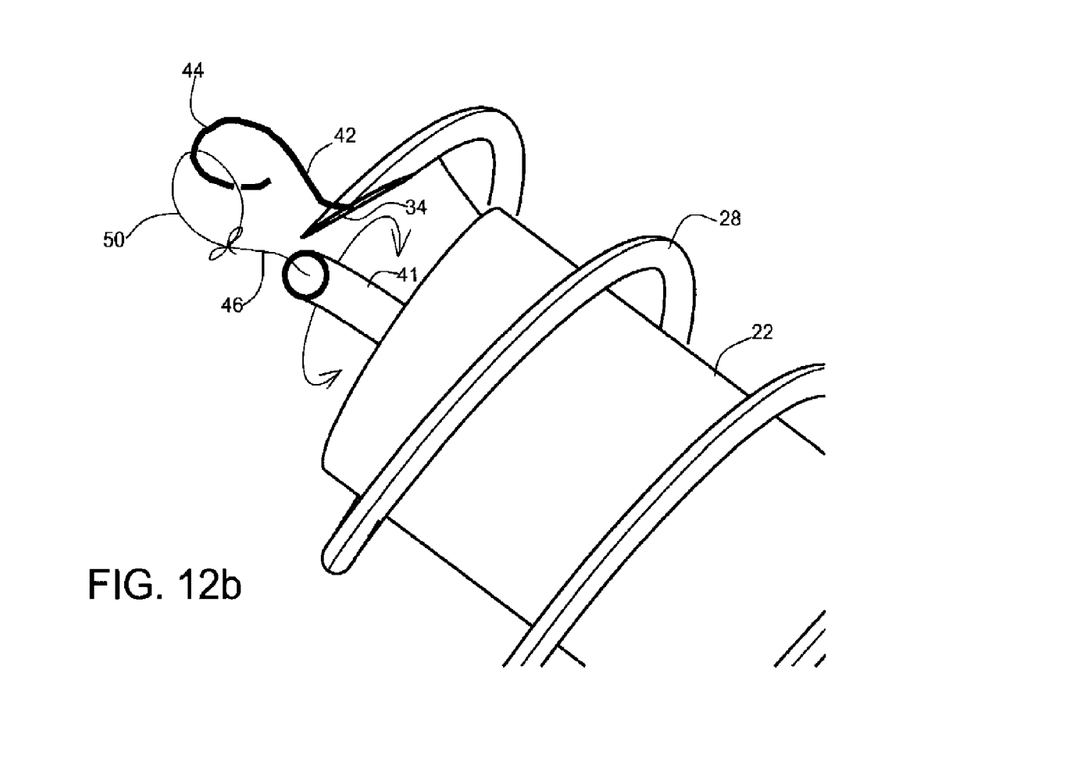

In FIGS. 11a-b, spiral needle driver 38 and second driver 48 are employed by the operator so as to manipulate first end 50 of suture thread 46 to become linked to suture hook 44 of guide wire 42. This action may be performed via counter rotation of one or both of drivers 38, 48 in the direction opposite the direction previously employed for advancement of guide wire 42 and suture thread 46. In FIG. 12a and the enlarged view 12b, suture thread 46 is shown linked to guide wire 42.

Figure 13:
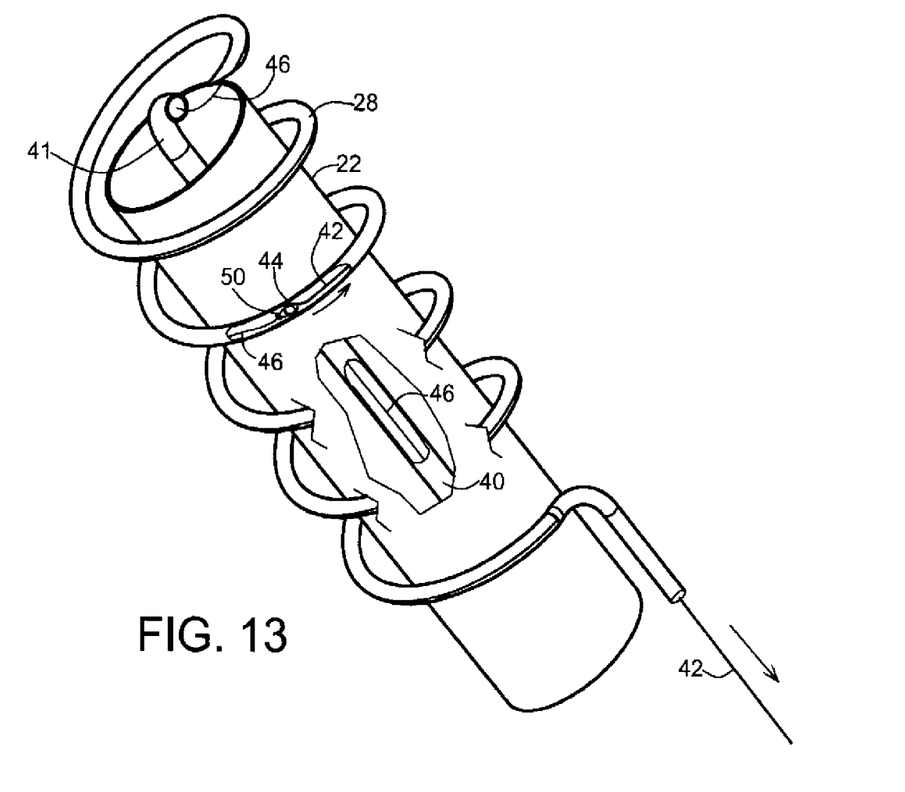
FIG. 13 is an enlarged and partially cut away view of the suturing device, as the suture thread is being drawn downward via the guide wire through the spiral needle.

In FIG. 13, after first end 50 of suture thread 46 has been linked with hook 44 of guide wire 42, guide wire 42 is retracted backwards through spiral needle 28 such that suture thread 46 becomes drawn through spiral needle 28. Subsequently, spiral needle 28 is itself withdrawn from around opening 24 and from apex 26 of the heart.

Figure 14:
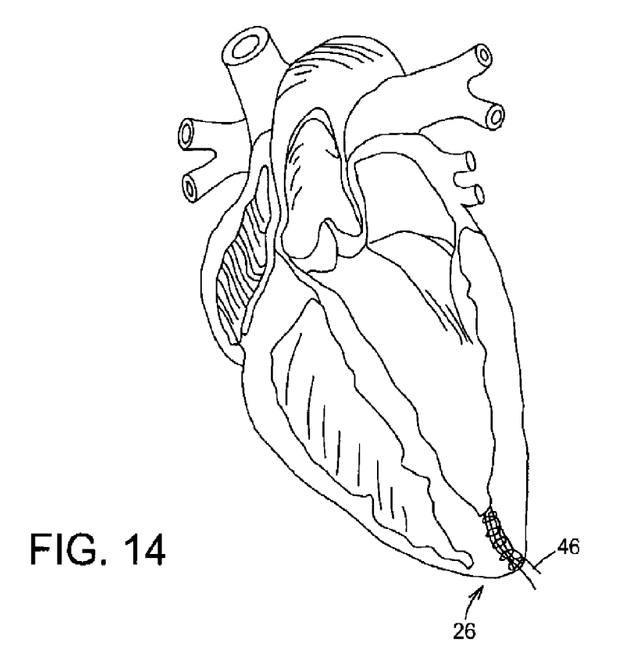
FIGS. 14-15 represent respectively, cutaway views of the human heart after the suture thread has been advanced through the spiral needle and after the suturing device has been withdrawn from the heart apex, with FIG. 14 showing the suture thread prior to tightening and FIG. 15 showing the suture thread after tightening.
Figure 15:
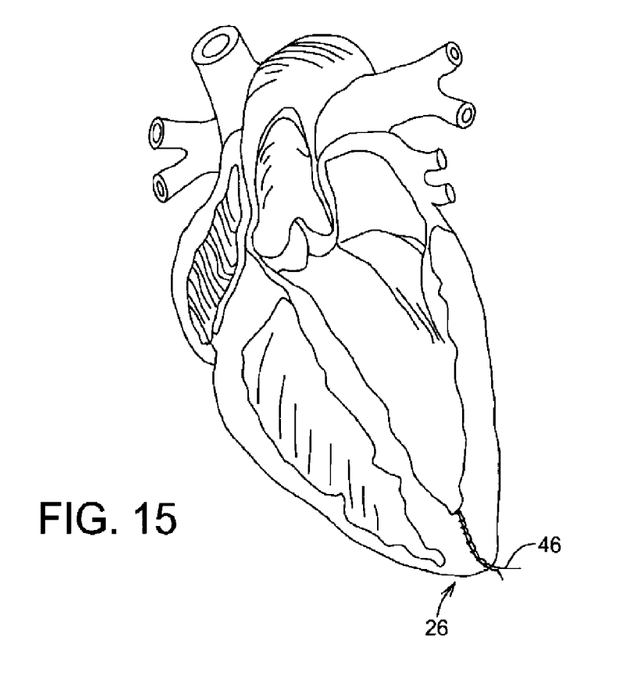

As spiral needle 28 is withdrawn from the suturing site by reverse rotation using driver 38, suture thread 46 remains at the site, in the configuration shown in FIG. 14, with one section of suture thread 46 looped around the other. The operator then ties the two free ends of the suture thread 46, tightening and joining the first end which is located in the center of the apical opening 24 and the second end located in the spiral opening cut by spiral needle 28. The operator may choose to form more than one knot.

This procedure provides a reduction in the risks, side effects, and recovery time for the suturing procedure. The device and method are relatively simple, and using radiology or any other suitable means, the surgeon can easily visualize the procedure, while it is being performed. The procedure itself requires only a few steps, and thus is relatively easy to learn to do. Unlike the common technique of surface suturing, a closure is provided throughout the heart apex wall, providing a stronger closure.

Having described the present invention with regard to certain specific embodiments thereof, it is to be understood that the description is not meant as a limitation, since further modifications may now suggest themselves to those skilled in the art, and it is intended to cover such modifications as fall within the scope of the appended claims.

The invention claimed is:

1. A suturing device for use with a delivery catheter in a transcatheter procedure, for closing an opening formed in body tissue, said suturing device comprising:
   a spiral needle having a hollow central core, a proximal end, and a distal end, said distal end terminating in a sharp point forming an aperture of said hollow core, for cutting a spiral passageway through body tissue surrounding said opening to be closed;
   a guide wire having a suture eye at one end thereof for receiving a suture thread at said distal end after said guide wire has been advanced through said hollow central core of said spiral needle; and
   a driver for rotatably advancing and retracting said spiral needle relative to said delivery catheter, wherein said driver is attached to said spiral needle and comprises an axial opening with an interior surface sized to rotatably interface entirely with an outer surface of said delivery catheter,
   wherein said driver comprises a second opening, located radially outside said axial opening, connected to the hollow core of said spiral needle, and
   wherein said second opening is sized for insertion of said guide wire and configured to pass said guide wire through said second opening into said hollow central core,
   such that when said device is rotatably advanced relative to said delivery catheter, a connection can be made between said suture thread and said suture eye of said guide wire, thus enabling formation of a spiral suture as said guide wire is retracted through said spiral needle and as said spiral needle is retracted.

2. The device of claim 1, wherein the device is configured for use in closing an opening formed in the apex of the heart during a transcatheter valve implantation procedure.

3. The device of claim 1 wherein the device is configured for use when said body tissue opening is formed by a lateral surgical incision.

4. The device of claim 1 wherein the device is configured for use when said body tissue opening is formed by an internal wound.

5. The device of claim 1 wherein said spiral needle is configured to surround said delivery catheter.

6. The device of claim 1 further comprising a hollow flexible tube for delivering said suture thread through said delivery catheter, said hollow tube having a curved distal end to direct said suture thread against said spiral needle for connection with said guide wire suture eye.

7. The device of claim 1, wherein said suture eye is formed by a hook.

8. The device of claim 6, wherein said suture device further comprises:
   a second driver attached to said hollow flexible tube,
   wherein said second driver comprises an axial opening sized for insertion of said suture thread and configured to pass said suture thread through said axial opening of said second driver and into said flexible tube, and wherein axial rotation of said second driver axially rotates the direction of said curved end of said flexible tube.

9. The device of claim 1, wherein said guide wire is slidably received within said hollow central core of said spiral needle such that said suture eye can be retracted through said spiral needle.

\* \* \* \* \*